United States Patent [19]
Simon et al.

[11] Patent Number: 6,118,845
[45] Date of Patent: Sep. 12, 2000

[54] SYSTEM AND METHODS FOR THE REDUCTION AND ELIMINATION OF IMAGE ARTIFACTS IN THE CALIBRATION OF X-RAY IMAGERS

[75] Inventors: David A. Simon; Kurt R. Smith, both of Boulder, Colo.

[73] Assignee: Surgical Navigation Technologies, Inc., Broomfield, Colo.

[21] Appl. No.: 09/106,109

[22] Filed: Jun. 29, 1998

[51] Int. Cl.$^7$ .................................................. G01N 23/04
[52] U.S. Cl. ............................................. 378/62; 378/207
[58] Field of Search ............................ 378/4, 8, 62, 98, 378/207, 901

[56] References Cited

U.S. PATENT DOCUMENTS

| | | | |
|---|---|---|---|
| Re. 35,025 | 8/1995 | Anderton | 378/101 |
| 1,576,781 | 3/1926 | Philips . | |
| 1,735,726 | 11/1929 | Bornhardt . | |
| 2,407,845 | 9/1946 | Nemeyer | 116/124 |
| 2,650,588 | 9/1953 | Drew | 128/92 |
| 2,697,433 | 12/1954 | Zehnder | 128/83 |
| 3,016,899 | 1/1962 | Stenvall | 128/348 |
| 3,017,887 | 1/1962 | Heyer | 128/348 |
| 3,061,936 | 11/1962 | Dobbeleer | 33/174 |
| 3,073,310 | 1/1963 | Mocarski | 128/303 |
| 3,294,083 | 12/1966 | Alderson | 128/2 |
| 3,367,326 | 2/1968 | Frazier | 128/92 |
| 3,577,160 | 5/1971 | White . | |
| 3,702,935 | 11/1972 | Carey et al. | 250/58 |
| 3,704,707 | 12/1972 | Halloran | 128/92 |
| 3,941,127 | 3/1976 | Froning | 128/215 |
| 4,037,592 | 7/1977 | Kronner . | |
| 4,117,337 | 9/1978 | Staats | 250/445 T |
| 4,202,349 | 5/1980 | Jones | 128/689 |
| 4,358,856 | 11/1982 | Stivender et al. | 378/167 |
| 4,403,321 | 9/1983 | Krüger . | |
| 4,418,422 | 11/1983 | Richter et al. . | |
| 4,485,815 | 12/1984 | Amplatz . | |

(List continued on next page.)

FOREIGN PATENT DOCUMENTS

| | | |
|---|---|---|
| 964149 | 3/1975 | Canada . |
| 350996 | 1/1990 | European Pat. Off. . |
| 0 581 704 A1 | 7/1993 | European Pat. Off. . |
| 79 04241 | 2/1979 | France . |
| 3042343 | 6/1982 | Germany . |
| WO 88/09151 | 12/1988 | WIPO . |
| WO 91/03982 | 4/1991 | WIPO . |
| WO 91/04711 | 4/1991 | WIPO . |
| WO 91/07726 | 5/1991 | WIPO . |
| WO 92/06645 | 4/1992 | WIPO . |
| WO 94/23647 | 10/1994 | WIPO . |
| WO 94/24933 | 11/1994 | WIPO . |
| WO 96/11624 | 4/1996 | WIPO . |
| WO 98/38908 | 9/1998 | WIPO . |

OTHER PUBLICATIONS

S. Schreiner, et al., "Accuracy assessment of a clinical biplane fluoroscope for three-dimensional measurements and targeting," Proceedings of SPIE, Image Display, vol. 3031, pp. 160–166, Feb. 23–25, 1997.

(List continued on next page.)

*Primary Examiner*—David V. Bruce
*Attorney, Agent, or Firm*—Finnegan, Henderson, Farabow, Garrett & Dunner, LLP

[57] ABSTRACT

Image processing operations are used to improve images that include visual artifacts generated by calibration markers used in intrinsic calibration of an x-ray image. Artifacts introduced by opaque or semi-transparent calibration markers may be completely or partially removed from the image. More particularly, artifacts caused by opaque calibration markers are removed by changing the pixels corresponding to the projections of the calibration markers to blend in with pixels surrounding the calibration markers. Artifacts may also be generated with semi-transparent calibration markers. These artifacts may be eliminated from the image, while leaving intact the underlying image, by subtracting a constant offset from each marker projection.

33 Claims, 12 Drawing Sheets

U.S. PATENT DOCUMENTS

| | | | |
|---|---|---|---|
| 4,543,959 | 10/1985 | Sepponen | 128/653 |
| 4,621,628 | 11/1986 | Bludermann . | |
| 4,625,718 | 12/1986 | Olerud et al. . | |
| 4,651,732 | 3/1987 | Frederick | 128/303 R |
| 4,653,509 | 3/1987 | Oloff et al. | 128/749 |
| 4,706,665 | 11/1987 | Gouda | 128/303 B |
| 4,722,056 | 1/1988 | Roberts et al. | 364/413 |
| 4,722,336 | 2/1988 | Kim et al. | 128/303 |
| 4,727,565 | 2/1988 | Ericson | 378/205 |
| 4,737,921 | 4/1988 | Goldwasser et al. | 364/518 |
| 4,750,487 | 6/1988 | Zanetti | 128/303 B |
| 4,764,944 | 8/1988 | Finlayson | 378/20 |
| 4,771,787 | 9/1988 | Wrister et al. | 128/660.03 |
| 4,791,934 | 12/1988 | Brunnett | 128/653 |
| 4,797,907 | 1/1989 | Anderton | 378/101 |
| 4,803,976 | 2/1989 | Frigg et al. | 128/92 |
| 4,821,206 | 4/1989 | Arora | 364/513 |
| 4,991,579 | 2/1991 | Allen | 128/653 R |
| 5,013,317 | 5/1991 | Cole et al. . | |
| 5,027,818 | 7/1991 | Bova et al. | 128/653 R |
| 5,030,222 | 7/1991 | Calandruccio et al. | 606/96 |
| 5,031,203 | 7/1991 | Trecha | 378/205 |
| 5,059,789 | 10/1991 | Salcudean | 250/206.1 |
| 5,079,699 | 1/1992 | Tuy et al. | 364/413.22 |
| 5,094,241 | 3/1992 | Allen | 128/653.1 |
| 5,097,839 | 3/1992 | Allen | 128/653.1 |
| 5,107,843 | 4/1992 | Aarnio et al. | 128/662.05 |
| 5,119,817 | 6/1992 | Allen | 128/653.1 |
| 5,142,930 | 9/1992 | Allen et al. | 74/469 |
| 5,178,164 | 1/1993 | Allen | 128/898 |
| 5,178,621 | 1/1993 | Cook et al. . | |
| 5,186,174 | 2/1993 | Schlondorff et al. | 128/653.1 |
| 5,198,877 | 3/1993 | Schulz | 356/375 |
| 5,211,164 | 5/1993 | Allen | 128/653.1 |
| 5,212,720 | 5/1993 | Landi et al. | 378/206 |
| 5,219,351 | 6/1993 | Teubner et al. | 606/130 |
| 5,249,581 | 10/1993 | Horbal et al. | 128/664 |
| 5,251,127 | 10/1993 | Raab | 364/413.13 |
| 5,295,483 | 3/1994 | Nowacki et al. | 128/660.03 |
| 5,299,254 | 3/1994 | Dancer et al. | 378/163 |
| 5,305,203 | 4/1994 | Raab | 364/413.13 |
| 5,309,913 | 5/1994 | Kormos et al. | 128/653.1 |
| 5,320,111 | 6/1994 | Livingston . | |
| 5,333,168 | 7/1994 | Fernandes et al. | 378/108 |
| 5,368,030 | 11/1994 | Zinreich et al. . | |
| 5,383,454 | 1/1995 | Bucholz | 128/653.1 |
| 5,389,101 | 2/1995 | Heilbrun et al. | 606/130 |
| 5,399,146 | 3/1995 | Nowacki et al. | 601/4 |
| 5,400,384 | 3/1995 | Fernandes et al. | 378/108 |
| 5,402,801 | 4/1995 | Taylor | 128/898 |
| 5,408,409 | 4/1995 | Glassman et al. . | |
| 5,426,683 | 6/1995 | O'Farrell, Jr. et al. | 378/197 |
| 5,426,687 | 6/1995 | Goodall et al. | 378/206 |
| 5,427,097 | 6/1995 | Depp . | |
| 5,442,674 | 8/1995 | Picard et al. | 378/20 |
| 5,446,548 | 8/1995 | Gerig et al. . | |
| 5,447,154 | 9/1995 | Cinquin et al. | 128/653.1 |
| 5,478,341 | 12/1995 | Cook et al. . | |
| 5,478,343 | 12/1995 | Ritter . | |
| 5,483,961 | 1/1996 | Kelly et al. | 128/653.1 |
| 5,490,196 | 2/1996 | Rudich et al. | 378/101 |
| 5,494,034 | 2/1996 | Schlondorff et al. | 128/653.1 |
| 5,503,416 | 4/1996 | Aoki et al. | 280/79.11 |
| 5,515,160 | 5/1996 | Schulz et al. | 356/241 |
| 5,517,990 | 5/1996 | Kalfas et al. | 128/653.1 |
| 5,531,227 | 7/1996 | Schneider | 128/653.1 |
| 5,531,520 | 7/1996 | Grimson et al. | 382/131 |
| 5,568,809 | 10/1996 | Ben-haim | 128/656 |
| 5,572,999 | 11/1996 | Funda et al. | 128/653.1 |
| 5,583,909 | 12/1996 | Hanover | 378/197 |
| 5,588,430 | 12/1996 | Bova et al. | 128/653.1 |
| 5,596,228 | 1/1997 | Anderton et al. | 297/714 |
| 5,603,318 | 2/1997 | Heilbrun et al. | 128/630 |
| 5,617,462 | 4/1997 | Spratt | 378/987 |
| 5,617,857 | 4/1997 | Chader et al. | 128/653.1 |
| 5,619,261 | 4/1997 | Anderton | 348/246 |
| 5,622,170 | 4/1997 | Schulz | 128/653.1 |
| 5,627,873 | 5/1997 | Hanover et al. | 378/197 |
| 5,630,431 | 5/1997 | Taylor | 128/897 |
| 5,638,819 | 6/1997 | Manwaring et al. | 128/653.1 |
| 5,642,395 | 6/1997 | Anderton et al. | 378/198 |
| 5,647,361 | 7/1997 | Damadian | 128/683.2 |
| 5,662,111 | 9/1997 | Cosman | 128/653.1 |
| 5,676,673 | 10/1997 | Ferre et al. | 606/130 |
| 5,682,886 | 11/1997 | Delp et al. | 128/653.1 |
| 5,690,108 | 11/1997 | Chakeres . | |
| 5,695,500 | 12/1997 | Taylor et al. | 606/130 |
| 5,695,501 | 12/1997 | Carol et al. | 606/130 |
| 5,711,299 | 1/1998 | Manwaring et al. | 128/653.1 |
| 5,748,767 | 5/1998 | Raab | 382/128 |
| 5,749,362 | 5/1998 | Funda et al. | 128/653.1 |
| 5,755,725 | 5/1998 | Druais | 606/130 |
| 5,769,789 | 6/1998 | Wang et al. . | |
| 5,769,861 | 6/1998 | Vilsmeier | 606/133 |
| 5,772,594 | 6/1998 | Barrick | 600/407 |
| 5,795,294 | 8/1998 | Luber et al. | 600/407 |
| 5,799,055 | 8/1998 | Peshkin et al. | 378/42 |
| 5,800,535 | 9/1998 | Howard, III | 623/10 |
| 5,802,719 | 9/1998 | O'Farrell, Jr. et al. | 29/897.35 |
| 5,823,958 | 10/1998 | Truppe | 600/426 |
| 5,828,725 | 10/1998 | Levinson | 378/98 |
| 5,833,608 | 11/1998 | Acker | 600/409 |
| 5,834,759 | 11/1998 | Glossop | 250/203.1 |
| 5,836,954 | 11/1998 | Heilbrun et al. | 606/130 |
| 5,848,967 | 12/1998 | Cosman | 600/426 |
| 5,851,183 | 12/1998 | Bucholz | 600/425 |
| 5,868,675 | 2/1999 | Henrion et al. | 600/424 |
| 5,871,445 | 2/1999 | Bucholz | 600/407 |
| 5,871,487 | 2/1999 | Warner et al. | 606/130 |
| 5,891,034 | 4/1999 | Bucholz | 600/426 |
| 5,891,157 | 4/1999 | Day et al. | 606/130 |
| 5,904,691 | 5/1999 | Barnett et al. | 606/130 |
| 5,920,395 | 7/1999 | Schulz | 356/375 |
| 5,921,992 | 7/1999 | Costales et al. | 606/130 |

OTHER PUBLICATIONS

A. Rougee, et al., "Geometrical Calibration of X–Ray Imaging Chains For Three–Dimensional Reconstruction," *Computerized Medical Imaging and Graphics*, vol. 17, Nos. 4/5, pp. 295–300, 1993.

B. Schueler, "Correction of image intensifier distortion for three–dimensional x–ray angiography," Proceedings of SPIE, Physics of Medical Imaging, vol. 2432, pp. 272–279, Feb. 26–27, 1995.

G. Champleboux, et al., "Accurate Calibration of Cameras and Range Imaging Sensors: the NPBS Method," Proceedings 1992 IEEE International Conference on Robotics and Automation, pp. 1552–1557, May 12–14, 1992.

Ch. Brack, et al., "Towards Accurate X–Ray–Camera Calibration in Computer–Assisted Robotic Surgery," CAR '96 Computer Assisted Radiology, Proceedings of the International Symposium on Computer and Communication Systems for Image Guided Diagnosis and Therapy, Paris, Jun. 1996, pp. 721–728.

D. Simon, "Fast and Accurate Shape–Based Registration," Carnegie Mellon University, Dec. 12, 1996.

P. Potamianos, et al., "Intra–operative imaging guidance for keyhole surgery methodology and calibration," Proceedings of the First International Symposium on Medical Robotics and Computer Assisted Surgery—Pittsburgh, PA—Sep. 22–24, 1994, pp.98–104.

P. Potamianos, et al., "Intra–operative registration for percutaneous surgery," Proceedings of the Second International Symposium on Medical Robotics and Computer Assisted Surgery—Baltimore, MD—Nov. 1995.

Foley, K.T., *The SteathStation™: Three–Dimensional Image–Interactive Guidance for the Spine Surgeon*, Spinal Frontiers, Apr. 1996, pp. 7–9.

Mazier, B., Lavellée, S., Cinquin, P., *Chirurgie de la Colonne Vertebrale Assistee par Ordinateur: Appication au Vissage Pediculaire*, Innov. Tech. Biol. Med., vol. 11, No. 5, 1990, pp. 559–566.

Mazier, B., Lavellee, S., Cinquin, P., *Computer Assisted Interventionist Imaging: Application to the Vertebral Column Surgery*, Annual International Conference of the IEEE Engineering in Medicine and Biology Society, vol. 12, No. 1, 1990, pp. 0430–0431.

Lavallée, S., Cinquin, P., Demongeot, J., Benabid, A.L., Marque, I., Djaid, M., *Computer Assisted Driving of a Needle into the Brain*, Proceedings of the International Symposium: CAR 89, pp. 416–420.

Lavallée, S., Cinquin, P., Dermongeot, J., Benabid, A L., Marque, I., Djaid, M., *Computer Assisted Interventionist Imaging: The Instance of Stereotactic Brain Surgery*, North–Holland Medinfo 89, Part 1, 1989, pp. 613–617.

Lavallée, S., *A New System for Computer Assisted Neurosurgery*, IEEE Engineering in Medicine & Biology Society 11$^{th}$ Annual International Conference, 1989, pp. 0926–0927.

Reinhardt, H.F., Landolt, H., *CT–Guided "Real Time" Stereotaxy*, ACTA Neurochirurgica, 1989.

Watanabe, E., Watanabe, T., Manaka, S., Mayanagi, Y., Takakura, K., *Three–Dimensional Digitizer (Neuronavigator): New Equipment for Computed Tomography–Guided Stereotaxic Surgery*, Surgical Neurology, vol. 27, No. 6, Jun. 1987, pp. 543–547.

Watanabe, H., *Neuronavigator*, Igaku–no–Ayumi, vol. 137, No. 6, May 10, 1986, pp. 1–4.

Roberts, D.W., Strohbehn, J.W., Hatch, J.F., Murray, W., Kettenberger, H., *A frameless stereotaxic integration of computerized tomographic imaging and the operating microscope*, J. Neurosurg., vol. 65, Oct. 1986, pp. 545–549.

Leksell, L., Jernberg, B., *Stereotaxis and Tomography—A Technical Note*, ACTA Neurochirurgica, vol. 52, 1980, pp. 1–7.

Hoerenz, P., *The Operating Microscope I. Optical Principles, Illumination Systems, and Support Systems*, Journal of Microsurgery, vol. 1, 1980, pp. 364–369.

Hounsfield, G.N., *Computerized transverse axial scanning (tomography): Part I. Description of system*, British Journal of Radiology, vol. 46, No. 552, Dec. 1973, pp. 1016–1022.

Lavallée, S., *VI Adaptation de la Methodologie a Quelques Applications Cliniques*, Chapitre VI, pp. 133–148.

André P. Guéziec et al., "Registration of Computer Tomography Data to a Surgical Robot Using Fluorscopy: A Feasibility Study," Computer Science/Mathematics, Sep. 27, 1996, 6 pages.

Ali Hamadeh et al., "Towards Automatic Registration Between CT and X–ray Images: Cooperation Between 3D/2D Registration and 2D Edge Detection," MRCAS '95, pp. 39–46.

L. Lemieux et al., "A Patient–to–Computer–Tomography Image Registration Method Based on Digitally Reconstructed Radiographs," Med. Phys. 21 (11), Nov. 1994, pp. 1749–1760.

Lisa M. Gottesfeld Brown et al., "Registration of Planar Film Radiographs with Computer Tomography," Proceedings of MMBIA, Jun. '96, pp. 42–51.

W. J. Viant et al., "A Computer Assisted Orthopaedic System for Distal Locking of Intramedullary Nails," Proc. of MediMEC '95, Bristol, 1995, pp. 86–91.

R. Phillips et al., "Image Guided Orthopaedic Surgery Design and Analysis," Trans Inst MC, vol. 17, No. 5, 1995, pp. 251–264.

R. Hofstetter et al., "Fluoroscopy Based Surgical Navigation—Concept and Clinical Applications," Computer Assisted Radiology and Surgery, 1997, pp. 956–960.

Jacques Feldmar et al., "3D–2D Projective Registration of Free–Form Curves and Surfaces," Rapport de recherche (Inria Sophia Antipolis), 1994, pp. 1–44.

C. Brack et al., "Accurate X–ray Based Navigation in Computer–Assisted Orthopedic Surgery," CAR '98, pp. 716–722.

Leo Joskowicz et al., "Computer–Aided Image–Guided Bone Fracture Surgery: Concept and Implementation," CAR '98, pp. 710–715.

Ali Hamadeh et al., "Automated 3–Dimensional Computer Tomographic and Fluoroscopic Image Registration," Computer Aided Surgery (1998), 3:11–19.

G. Selvik, et al., "A Roentgen Stereophotogrammetric System," Acta Radiologica Diagnosis, 1983, pp. 343–352.

Pascal Phillippe Sautot, "Vissage Pediculaire Assiste Par Ordinateur," Sep. 20, 1994.

Stephane Lavellee, et al., "Image guided operating robot: a clinical application in stereotactic neurosurgery," Proceedings of the 1992 IEEE Internation Conference on Robotics and Automation, May 1992, pp. 618–624.

P. Cinquin, et al., "Computer Assisted Medical Interventions," IEEE Engineering in Medicine and Biology, May/Jun. 1995, pp. 254–263.

Ali Hamadeh, et al., "Kinematic Study of Lumbar Spine Using Functional Radiographies and 3D/2D Registration," TIMC UMR 5525—IMAG.

S.Lavalle, et al., "Computer Assisted Spine Surgery: A Technique For Accurate Transpedicular Screw Fixation Using CT Data and a 3–D Optical Localizer," TIMC, Faculte de Medecine de Grenoble.

Foley, K.T., Smith, K.R., Bucholz, R.D., *Image–guided Intraoperative Spinal Localization*, Intraoperative Neuroprotection, Chapter 19, 1996, pp. 325–340.

Henderson, J.M., Smith, K.R., Bucholz, R.D., *An Accurate and Ergonomic Method of Registration for Image–guided Neurosurgery*, Computerized Medical Imaging and Graphics, vol. 18, No. 4, Jul.–Aug. 1994, pp. 273–277.

Lavallée, S. Brunie, L., Mazier, B., Cinquin, P., *Matching of Medical Images for Computed and Robot Assisted Surgery*, IEEE EMBS, Orlando, 1991.

Smith, K.R., Bucholz, R.D., *Computer Methods for Improved Diagnostic Image Display Applied to Stereotactic Neurosurgery*, Automedical, vol. 14, 1992, pp. 371–382.

Adams, L., Knepper, A., Krybus, W., Meyer–Ebrecht, D., Pfeifer, G., Ruger, R., Witte, M., *Aide au Reperage Tridimensional pour la Chirurgie de la Base du Crane*, Innov. Tech. Biol. Med., vol. 13, No. 4, 1992, pp. 409–424.

Colchester, A.C.F., Hawkes, D.J., *Information Processing in Medical Imaging*, Lecture Notes in Computer Science, 12$^{th}$ International Conference, IPMI, Jul. 1991, pp. 136–141.

Lavallée, S. Szeliski, R., Brunie, L., *Matching 3–D Smooth Surfaces with Their 2–D Projections usind 3–D Distance Maps*, SPIE, vol. 1570, Geometric Methods in Computer Vision, 1991, pp. 322–336.

Clarysse, P., Gibon, D., Rousseau, J., Blond, S., Vasseur, C., Marchandise, X., *A Computer–Assisted System for 3–D Frameless Localization in Stereotaxic MRI*, IEEE Transactions on Medical Imaging, vol. 10, No. 4, Dec. 1991, pp. 523–529.

Champleboux, G., *Utilisation de Fonctions Splines pour la Mise au Point D'un Capteur Tridimensionnel sans Contact*, Quelques Applications Medicales, Jul. 1991.

Pelizzari, C.A., Chen, G.T.Y., Spelbring, D.R., Weichselbaum, R.R., Chen, C., *Accurate Three–Dimensional Registration of CT, PET, and/ro MR Images of the Brain*, Journal of Computer Assisted Tomography, Jan./Feb. 1989, pp. 20–26.

Lavellée, S., Cinquin, P., Demongeot, J., Benabid, A.L., Marque, I. Djaïd, M., *Computer Assisted Interventionist Imaging: The Instance of Stereotactic Brain Surgery*, North–Holland Medinfo 89, Part 1, 1989, pp. 613–617.

Lavallee, S. Cinquin, P., Demongeot, J., Benabid, A.L., Marque, I., Djaid, M., *Computer Assisted Driving of a Needle into the Brain*, Proceedings of the International Symposium CAR '89, Computer Assisted Radiology, 1989, pp. 416–420.

Lavin, D.N., Hu, X., Tan, K.K., Galhotra, S., Pelizzari, C.A., Chen, G.T.Y., Beck, R.N., Chen, C., Cooper, M.D., Mullan, J.F., Hekmatpanah, J., Spire, J., *The Brain: Integrated Three–dimensional Display of MR and PET Images*, Radiology, vol. 172, No. 3, Sep. 1989, pp. 783–789.

Gonzalez, R.C., *Digital Image Fundamentals*, Digital Image Processing, Second Edition, 1987, pp. 52–54.

Pelizzari, C.A., Chen, G.T.Y., Halpern, H., Chen, C.T., Cooper, M.D., *No. 528—Three Dimensional Correlation of PET, CT and MRI Images*, The Journal of Nuclear Medicine, vol. 28, No. 4, Apr. 1987, p. 682.

Foley, J.D., Van Dam, A., *Fundamentals of Interactive Computer Graphics*, The Systems Programming Series, Chapter 7, Jul. 1984, pp. 245–266.

Hatch, J.F., *Reference–Display System for the Integration of CT Scanning and the Operating Microscope*, Thesis, Thayer School of Engineering, Oct. 1984, pp. 1–189.

Kelly, P.J., Kall, B., Goerss, S., Alker, G.J., Jr., *Precision Resection of Intra–Axial CNS Lesions by CT–Based Stereotactic Craniotomy and Computer Monitored $CO_2$ Laser*, Acta Neurochirurgica, vol. 68, 1983, pp. 1–9.

Gildenberg, P.L., Kaufman, H.H., Murthy, K.S., *Calculation of Stereotactic Coordinates from the Computed Tomographic Scan*, Neurosurgery, vol. 10, No. 5, May 1982, pp. 580–586.

Batnitzky, S., Price, H.I., Lee, K.R., Cook, P.N., Cook, L.T., Fritz, S.L., Dwyer, S.J., Watts, C., *Three–Dimensional Computer Reconstructions of Brain Lesions from Surface Contours Provided by Computed Tomography: A Prospectus*, Neurosurgery, vol. 11, No. 1, Part 1, 1982, pp. 73–84.

Rosenbaum, A.E., Lunsford, L.D., Perry, J.H., *Computerized Tomography Guided Sterotaxis: A New Approach*, Applied Neurophysiology, vol. 43, No. 3–5, 1980, pp. 172–173.

Jacques, S., Sheldon, C.H., McCann, G.D., *A Computerized Microstereotactic Method to Approach, 3–Dimensionally Reconstruct, Remove and Adjuvantly Treat Small CNS Lesions*, Applied Neurophysiology, vol. 43, 1980, pp. 176–182.

Jacques, S., Sheldon, C.H., McCann, G.D., Freshwater, D.B., Rand, R., *Computerized three–dimensional stereotaxic removal of small central nervous system lesion in patients*, J. Neurosurg., vol. 53, Dec. 1980, pp. 816–820.

Shelden, C.H., McCann, G., Jacques, S., Lutes, H.R., Frazier, R.E., Katz, R., Kuki, R., *Development of a computerized microstereotaxic method for localization and removal of minute CNS lesions under direct 3–D vision*, J. Neurosurg., vol. 52, 1980, pp. 21–27.

E. Frederick Barrick, "Journal of Orthopaedic Trauma: Distal Locking Screw Insertion Using a Cannulated Drill Bit: Technical Note," Raven Press, vol. 7, No. 3, 1993, pp. 248–251.

Bouazza–Marouf et al.; "Robotic–Assisted Internal Fixation of Femoral Fractures", IMECHE. pp. 51–58 (1995).

Frederick et al., "Prophylactic Intramedullary Fixation of the Tibia for Stress Fracture in a Professional Athlete," *Journal of Orthopaedic Trauma*, vol. 6, No. 2, pp. 241–244 (1992).

Frederick et al., "Technical Difficulties with the Brooker–Wills Nail in Acute Fractures of the Femur," *Journal of Orthopaedic Trauma*, vol. 6, No. 2, pp. 144–150 (1990).

PCT International Search Report, PCT/US99/14565, Oct. 20, 1999.

Jürgen Weese, et al., "*An Approach to 2D/3D Registration of a Vertebra in 2D X–ray Fluoroscopies with 3D CT Images*," First Joint Conference Computer Vision, Virtual Reality and Robotics in Medicine and Med. Robotics and Computer–ssisted Surgery, Grenoble, Frances, pp. 119–128 (Mar. 19–22, 1997).

Cinquin, P., et al., "Computer Assisted Medical Interventions," pp. 63–65 (Sep. 1989).

SYSTEM AND METHODS FOR THE REDUCTION AND ELIMINATION OF IMAGE ARTIFACTS IN THE CALIBRATION OF X-RAY IMAGERS

FIELD OF THE INVENTION

This invention relates generally to x-ray imaging systems, and more specifically, to the calibration of x-ray imaging systems.

BACKGROUND OF THE INVENTION

Modern diagnostic medicine has benefitted significantly from radiology, which is the use of radiation, such as x-rays, to generate images of internal body structures. In general, to create an x-ray image, x-ray beams are passed through the body and absorbed, in varying amounts, by tissues in the body. An x-ray image is created based on the relative differences in the transmitted x-ray intensities.

FIG. 1A is a diagram illustrating a fluoroscopic C-arm x-ray imaging device. Imaging device 100 includes C-arm 103 attached to mobile base 102. X-ray source 105 is located at one end of C-arm 103 and x-ray receiving section 106 is located at the other end of C-arm 103. Receiving section 106 generates an image representing the intensities of received x-rays. Typically, receiving section 106 comprises an image intensifier that converts the x-rays to visible light and a charge coupled device (CCD) video camera that converts the visible light to digital images.

Images taken at the mobile base 102 are transmitted to control unit 120 for analysis. In particular, control unit 120 typically provides facilities for displaying, saving, digitally manipulating, or printing a hard copy of the received images. Control unit 120 additionally includes controls for controlling base unit 102.

In operation, the patient is positioned in area 110, between the x-ray source 105 and the x-ray receiving section 106. In response to an operator's command input at control unit 120, x-rays emanating from source 105 pass through patient area 110 and into receiving section 106, which generates a two-dimensional image of the patient.

Although each individual image taken by base unit 102 is a two-dimensional image, techniques are known in the art through which multiple two-dimensional images taken from multiple perspectives can be used to infer the three-dimensional location of an anatomical projection. To change image perspective, C-arm 103 rotates as shown, for example, in FIG. 1B. By taking multiple two-dimensional images of point 124, but from different perspectives, the three-dimensional position of point 124 may be determined.

Raw images generated by receiving section 106 tend to suffer from undesirable distortion caused by a number of factors, including inherent image distortion in the image intensifier and external electromagnetic fields. An example of a true and a distorted image is shown in FIG. 2. Checkerboard 202 represents the true image of a checkerboard shaped object placed in image taking area 110. The image taken by receiving section 106, however, suffers significant distortion, as illustrated by distorted image 204.

Intrinsic calibration, which is the process of correcting image distortion in a received image and learning the projective geometry of the imager, involves placing "calibration markers" in the path of the x-ray, where a calibration marker is an object opaque to x-rays. The calibration markers are rigidly arranged in predetermined patterns in one or more planes in the path of the x-rays and are visible in the recorded images.

Because the true relative position of the calibration markers in the recorded images is known, control unit 120 is able to calculate an amount of distortion at each pixel in the image (where a pixel is a single point in the image). Accordingly, control unit 120 can digitally compensate for the distortion in the image and generate a distortion-free, or at least a distortion improved image. A more detailed explanation of a method for performing intrinsic calibration is described in U.S. Pat. No. 5,442,674 to Picard et al, the contents of which are incorporated by reference herein.

A notable disadvantage in the conventional method of compensating for image distortion, as described above, is that although there is significantly less distortion in the image, projections of the calibration markers are present in the image. This is undesirable, as the projections of the markers may occlude important portions of the patient's anatomy and/or act as a visual distraction that prevents the clinician from concentrating on important features of the image.

There is, therefore, a need in the art to improve the intrinsic calibration process.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, a first aspect consistent with the present invention includes a method for causing a computer processor to perform the steps of: storing a digital image representing anatomy of a patient, the digital image including representations of calibration markers that at least partially occlude portions of the patient anatomy; and performing image processing operations on the digital image to de-emphasize the representations of the calibration markers.

Additional aspects of the present invention, related to the first aspect, are directed to a computer readable medium and a computer system.

A second aspect of the present invention is directed to a medical imaging system comprising a combination of elements, including: an x-ray source for generating x-rays; semi-transparent calibration markers positioned in a path of the x-rays; and an x-ray receiving device for receiving the generated x-rays and deriving a digital image representing objects through which the generated x-rays have passed, the digital image including representations of the calibration markers. A processor is coupled to the x-ray receiving device and performs image processing operations on the digital image, the digital processing operations removing distortion from the image by performing intrinsic calibration on the image based on projections of the semi-transparent calibration markers in the image.

A third aspect of the present invention is directed to a method of creating an image of an object. The method comprises the steps of: transmitting x-rays in a path including a target object and calibration markers arranged in a predetermined pattern; receiving the transmitted x-rays; deriving a digital image representing the object and the calibration markers; and de-emphasizing the representations of the calibration markers in the digital image.

Additional aspects of the present invention, related to the third aspect, are directed to a computer readable medium and a computer system.

BRIEF DESCRIPTION OF THE DRAWINGS

The accompanying drawings, which are incorporated in and constitute a part of this specification, illustrate several embodiments consistent with this invention and, together with the description, help explain the principles of the invention. In the drawings.

DETAILED DESCRIPTION

As described herein, image processing operations are used to improve images that include visual artifacts generated by calibration markers used in intrinsic calibration of the image. Artifacts introduced by opaque or semi-transparent calibration markers may be completely or partially removed from the image.

Referring to the accompanying drawings, detailed description of embodiments consistent with the present invention will now be described.

System Overview

Methods consistent with the present invention may be implemented on images taken with an x-ray imaging device in which intrinsic image calibration is implemented. One such imaging device is the "Series9600 Mobile Digital Imaging System," from OEC Medical Systems, Inc., of Salt Lake City, Utah. The "Series9600 Mobile Digital Imaging System" is structurally similar to imaging system 100. Alternatively, methods consistent with the present invention may be implemented on images at a computer system not associated with the imaging device.

Figure 1A:
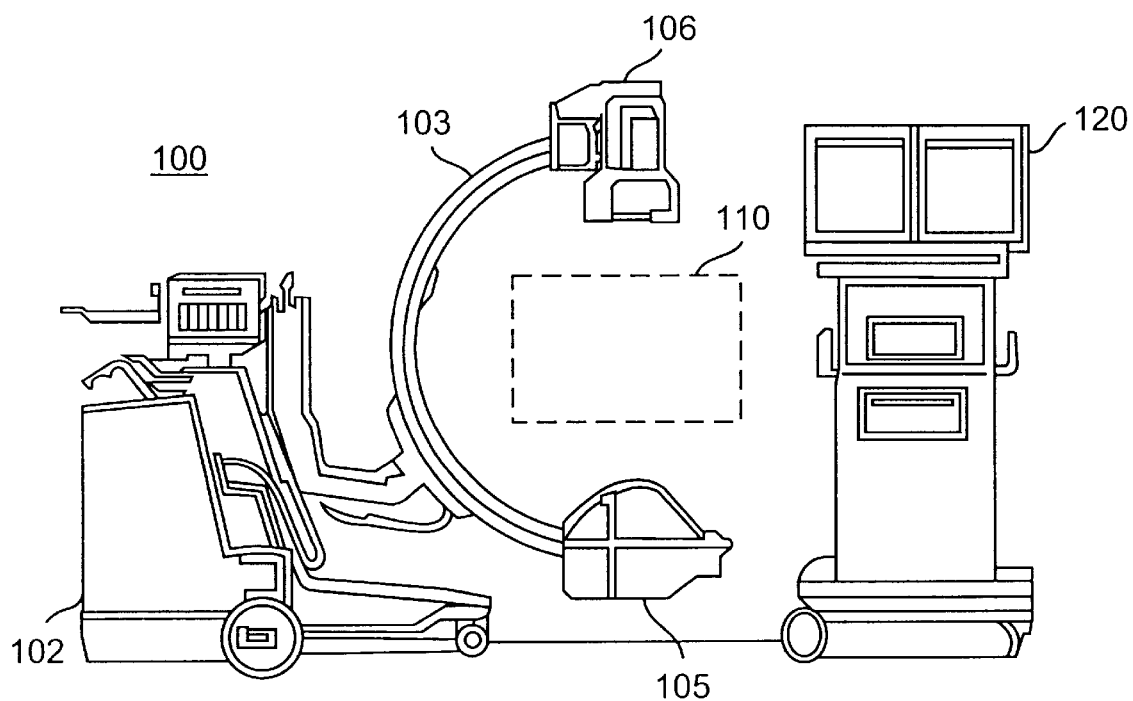
FIGS. 1A and 1B are diagrams illustrating a fluoroscopic C-arm x-ray imaging device.
Figure 1B:
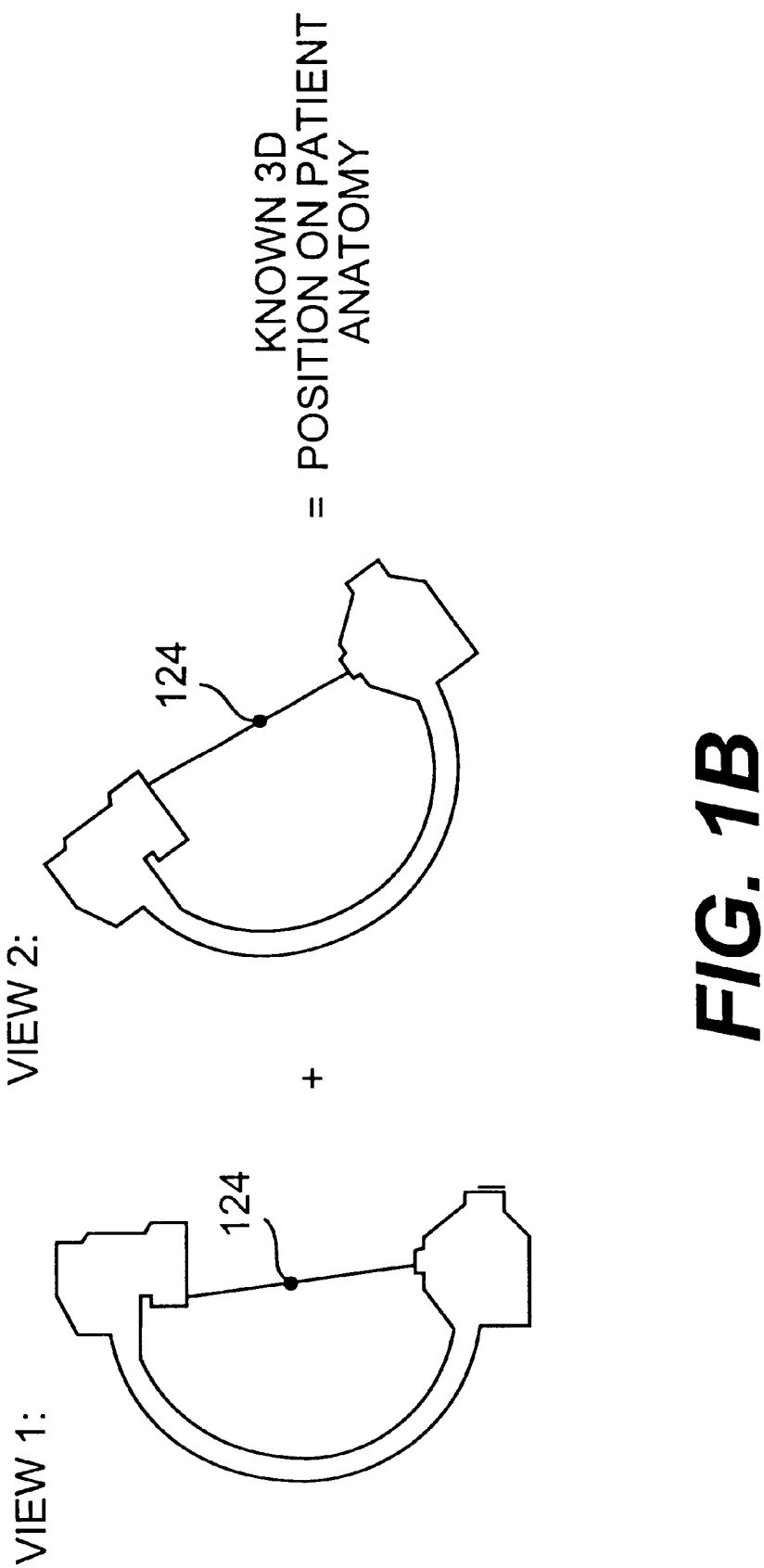
Figure 2:
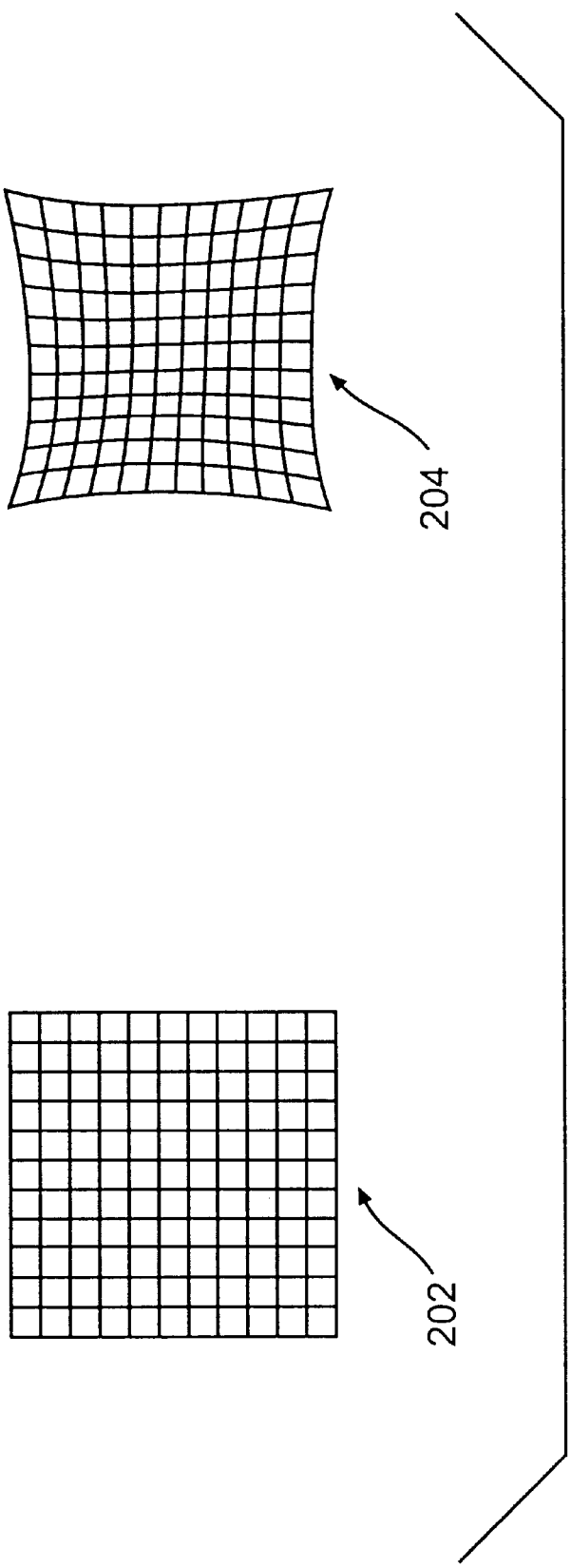
FIG. 2 is a diagram illustrating a true and a distorted image taken with a fluoroscopic C-arm x-ray imaging device.
Figure 3:
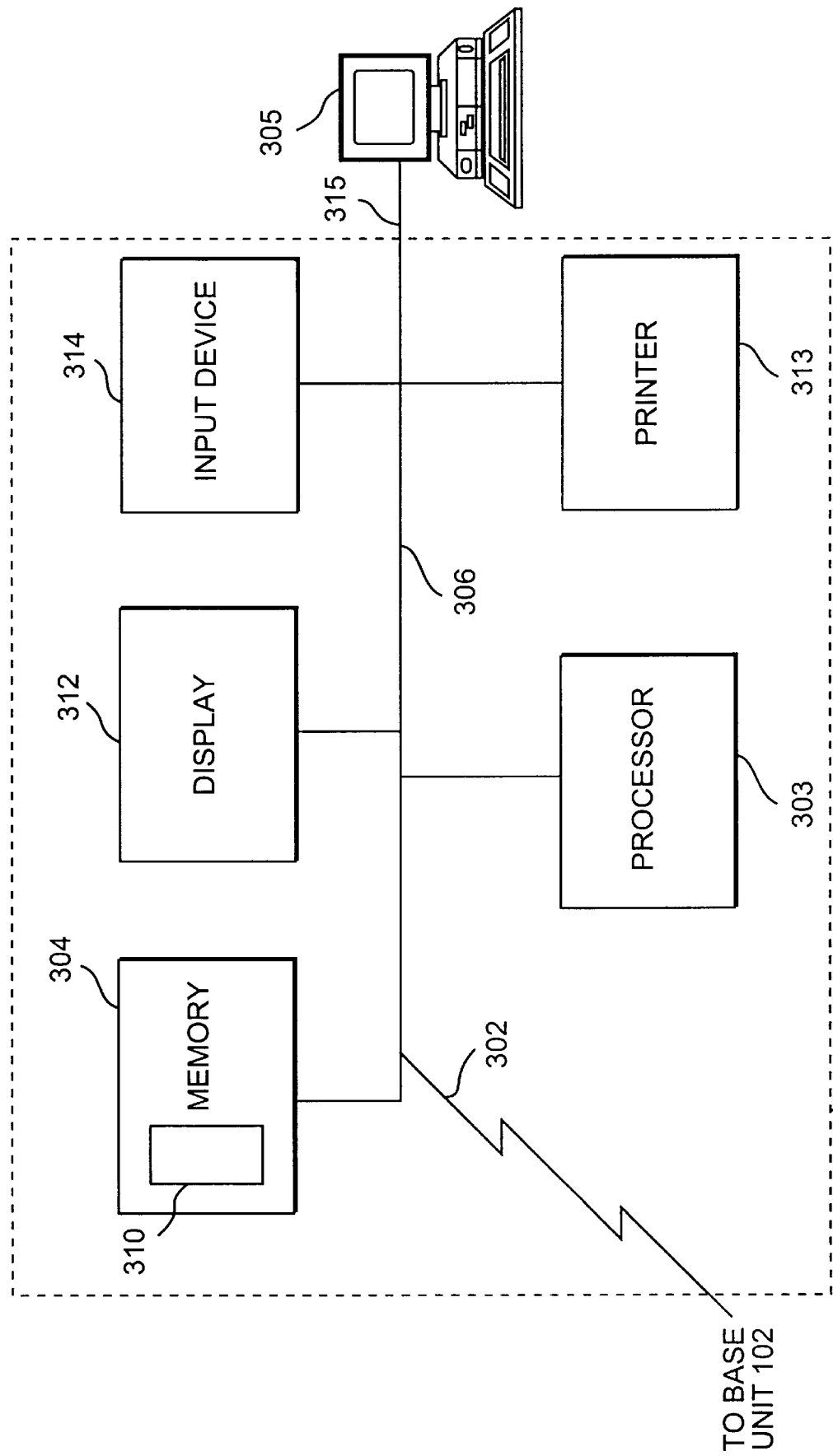
FIG. 3 is a block diagram illustrating a control unit of an imaging device.

FIG. 3 is a block diagram illustrating control unit 120 in more detail. Communications between base unit 102 and control unit 120 are performed via transmission medium 302, which may be, for example, a radio or cable link. Digital images may be received from base unit 102 and commands transmitted to base unit 102. Control unit 120 may include an additional external connection, such as network connection 315. Through network connection 315, data, such as images stored in memory 304, may be transmitted to additional computing resources, such as computer 305.

Control unit 120 further comprises a computer processor 303 and a memory 304 coupled to processor 303 through a bus 306. Processor 303 fetches computer instructions from memory 304 and executes those instructions. Processor 303 also (1) reads data from and writes data to memory 304, (2) sends data and control signals through bus 306 to one or more peripheral output devices 312 and 313; and (3) receives data and control signals through bus 306 from input device(s) 314.

Memory 304 can include any type of computer memory, including, without limitation, random access memory (RAM), read-only memory (ROM), and storage devices that include storage media such as magnetic and/or optical disks. Memory 304 includes a computer process 310 that processor 303 executes. A computer process in this description is a collection of computer instructions and data that collectively define a task performed by control unit 120.

Input device 314 is used by an operator to enter commands to control unit 120. The commands may be executed directly by control unit 120 or transmitted to base unit 102. Input device 314 may be, for example, a keyboard, a pointing device such as a mouse, or a combination thereof.

Output devices 312 and 313 are preferably a display and a printer, respectively. Display 312 is typically used to exhibit images taken by base unit 102 and printer 313 is used to create hard copies of the images.

In operation, images stored in memory 304 may be processed by processor 303 to perform various image processing operations. For example, processor 303 may perform intrinsic calibration on an image or generate the location of a three-dimensional point from a series of two-dimensional images. Consistent with the present invention, processing section 303 also removes artifacts caused by calibration markers used in the intrinsic calibration process. Computer 305, instead of processing section 303, may alternatively perform image processing operations consistent with the present invention.

The above-described architecture of control unit 120 is exemplary only. One of ordinary skill in the art will recognize that many modifications could be made to the described architecture and still achieve the described functionality.

Intrinsic Calibration

As previously discussed, intrinsic calibration uses calibration markers placed at fixed, predetermined positions in the x-ray imaging path to either obtain an image transformation that removes distortion from the original image generated by receiving section 106 or to learn the projective geometry of the imager (i.e., to discern how a pixel in the image projects into three-dimensional space). Typically, each calibration marker is a three-dimensional shape that appears in the image as a two-dimensional object, although calibration markers can also be constructed using thin films that are essentially two-dimensional in nature. Many possible shapes, such as spheres and cylindrical rods can be used to implement the calibration markers. Spheres appear in the two-dimensional image as circles and cylindrical rods appear as lines. Throughout this disclosure, spherical calibration markers are illustrated, although one of ordinary skill in the art will recognize that calibration markers of any shape could be used.

A typical C-arm calibration target contains a large set of calibration markers (e.g., 25+) with the markers positioned over one or more depth planes.

Artifact Reduction

Consistent with a first aspect of the present invention, artifacts introduced into an x-ray image by radio-opaque markers are reduced.

Figure 4:
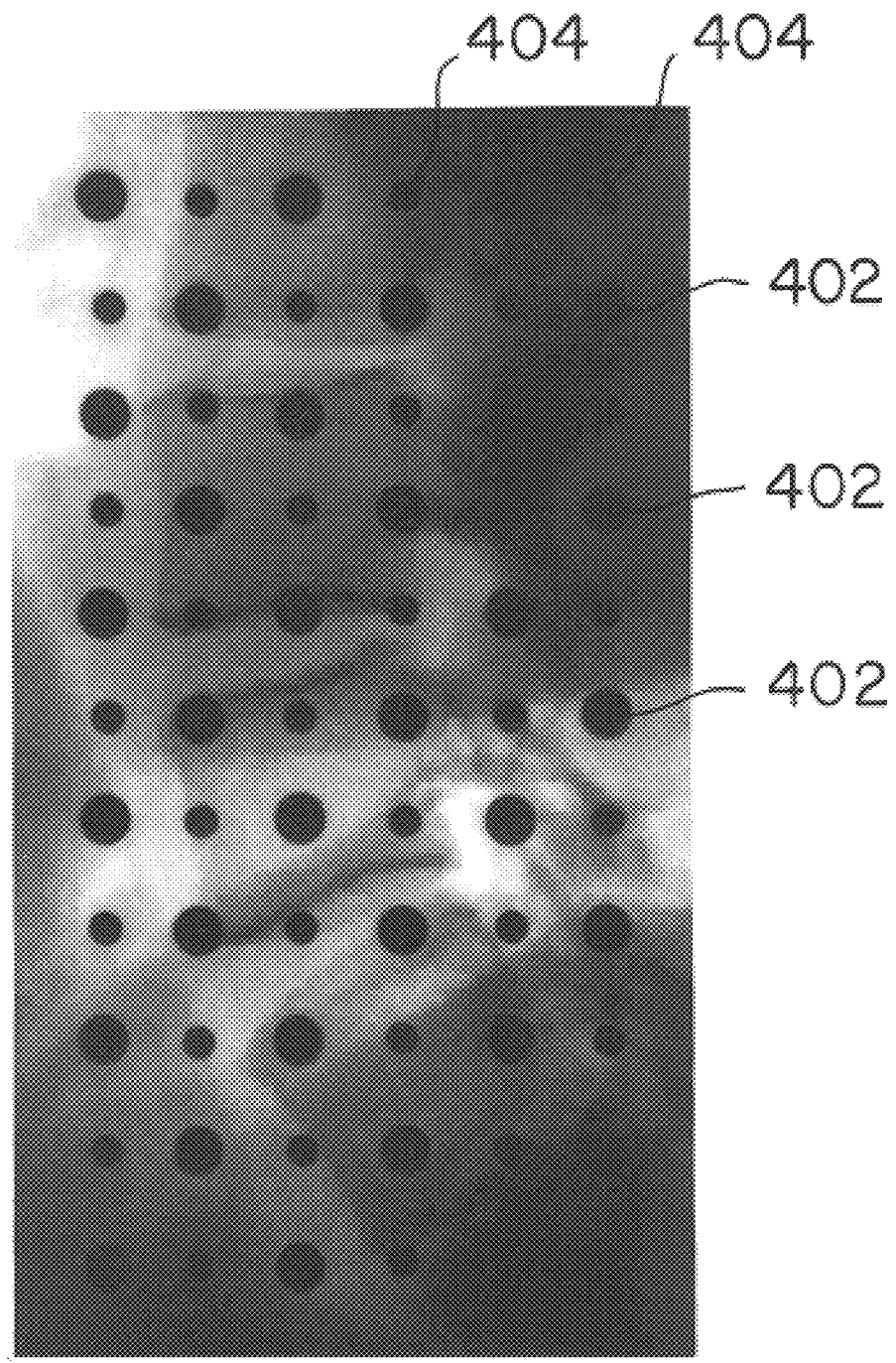
FIG. 4 is an image illustrating two-dimensional circular artifacts projected from spherical calibration markers.

FIG. 4 is an image having two-dimensional circular artifacts projected from spherical calibration markers. Two different calibration marker patterns were used to generate image 400. Large circles 402 represent a first spherical pattern of the calibration markers and smaller circles 404 represent a second spherical pattern of the calibration markers. Preferably, each spherical pattern is rigidly fixed in a separate plane traversed by the x-rays. As shown, markers 402 and 404 were opaque to the x-rays used to take the image, thus the two-dimensional projection of the markers appears as solid black circles.

Figure 5:
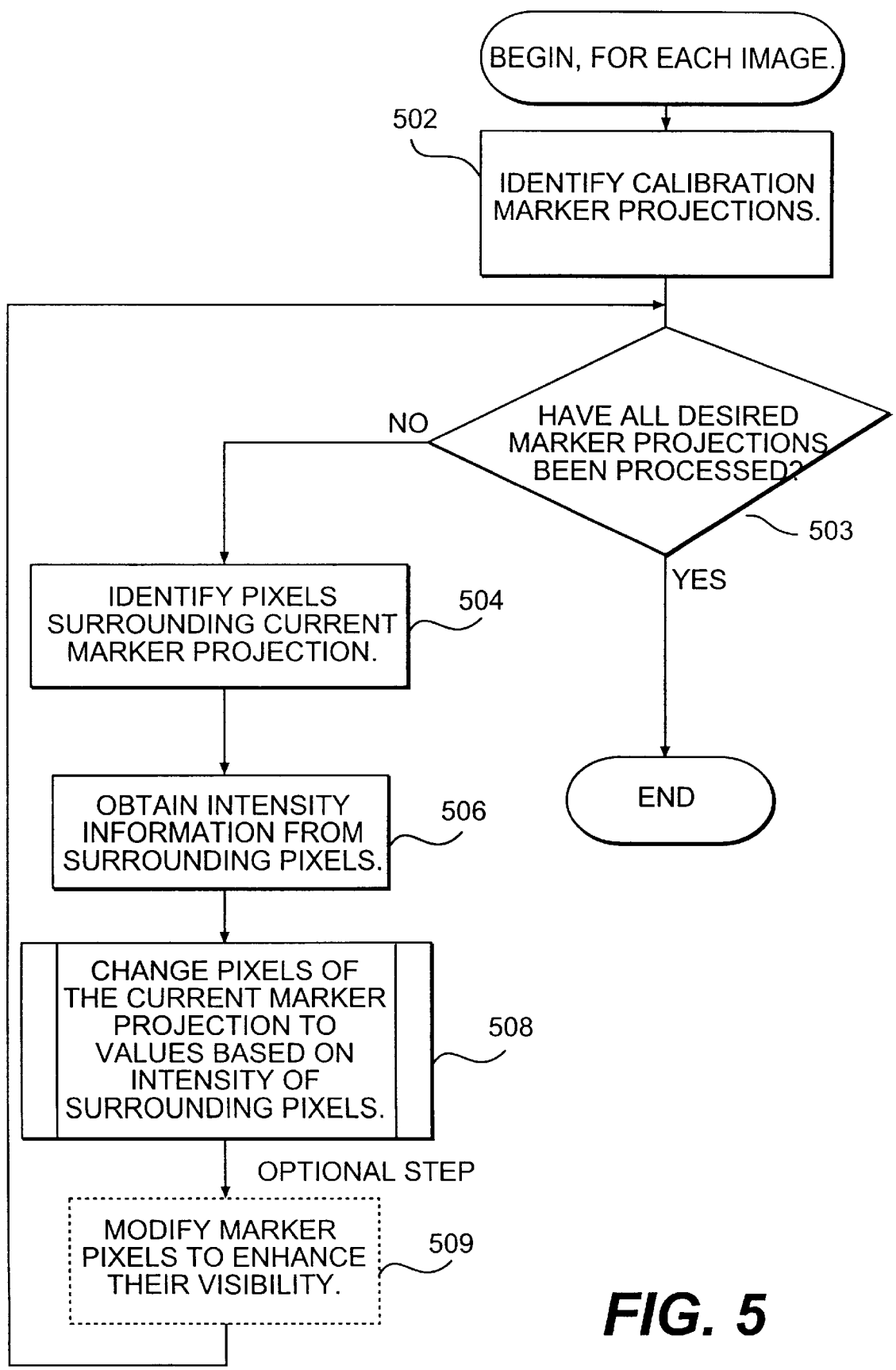
FIG. 5 is a flow chart of image processing methods consistent with the present invention for reducing the artifacts caused by calibration markers.

FIG. 5 is a flow chart of image processing methods consistent with the present invention for reducing the artifacts caused by calibration markers, such as artifacts 402 and 404 of image 400. The methods illustrated in FIG. 5 may be performed after a received image has been intrinsically calibrated to reduce image distortion.

For each digitized image that is to be processed, processor 303 begins by identifying the calibration marker projections in the image (step 502). As the shape, general pixel intensity, and relative position of the markers are known a priori, detection of the marker projections is a straightforward image processing operation well within the skill of one of ordinary skill in the art, and therefore will not be described further. Identification of the marker projections classifies the image pixels into those corresponding to the marker projections and those corresponding to anatomy or other non-marker objects.

For each marker projection in the image, processor 303 identifies pixels surrounding the identified marker artifacts, (steps 503 and 504), and reads the values (intensities) of the surrounding pixels (step 506). Finally, the processor changes the pixel values of the marker projections to values based on that of the pixels surrounding the marker (step 508). The modified pixels of the marker projections tend to blend in more smoothly with the actual image, thereby reducing the visual distraction caused by the marker artifacts.

Because the new marker projection values are only estimates of the intensities of the true underlying image data, it is possible that the new marker projection values will not accurately reflect the true image and will mislead the clinician. Accordingly, processor 303 may modify the marker pixels so that they are visible to the clinician but yet are still visibly less distracting than the original marker projections (optional step 509). Preferably, this step is achieved by supplementing the new marker projection values with a small constant offset (e.g., 5% of the maximum pixel value), thus causing the new marker projections to be visibly distinct but not visually distracting.

Figure 6:
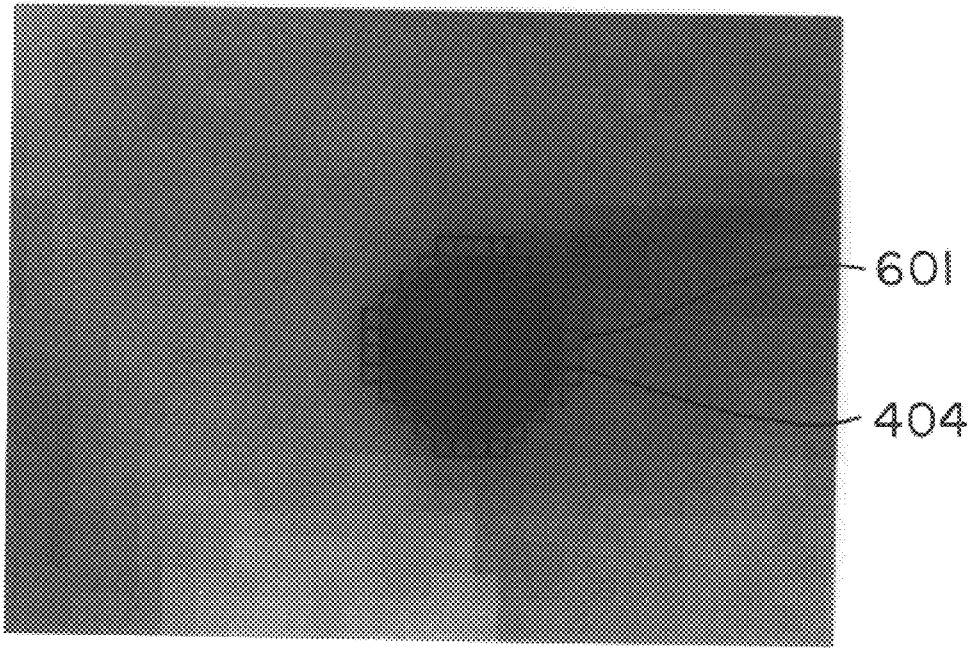
FIG. 6 is an image of an expanded view of a calibration marker projection.

FIG. 6 is an image of an expanded view of one of calibration marker projections 404. Small squares 601 highlight pixels defined as surrounding pixels in step 504. As shown, the "surrounding pixels" are not necessarily limited to just those pixels that immediately border marker projection 404, but may include additional neighboring pixels. For example, the surrounding pixels may include all the pixels with a certain radius of the outer border of the marker projection (e.g., a radius of five pixels) or all the non-marker pixels within a square aligned with the center of the marker projection.

There are many possible approaches to appropriately modifying the pixel values within the marker projections as performed in step 508. The best approach used by processor 303 in any particular situation may vary depending on the circumstances, and may be selectable by the user or selected automatically by processor 303. Exemplary ones of these approaches will now be discussed.

Figure 7A:
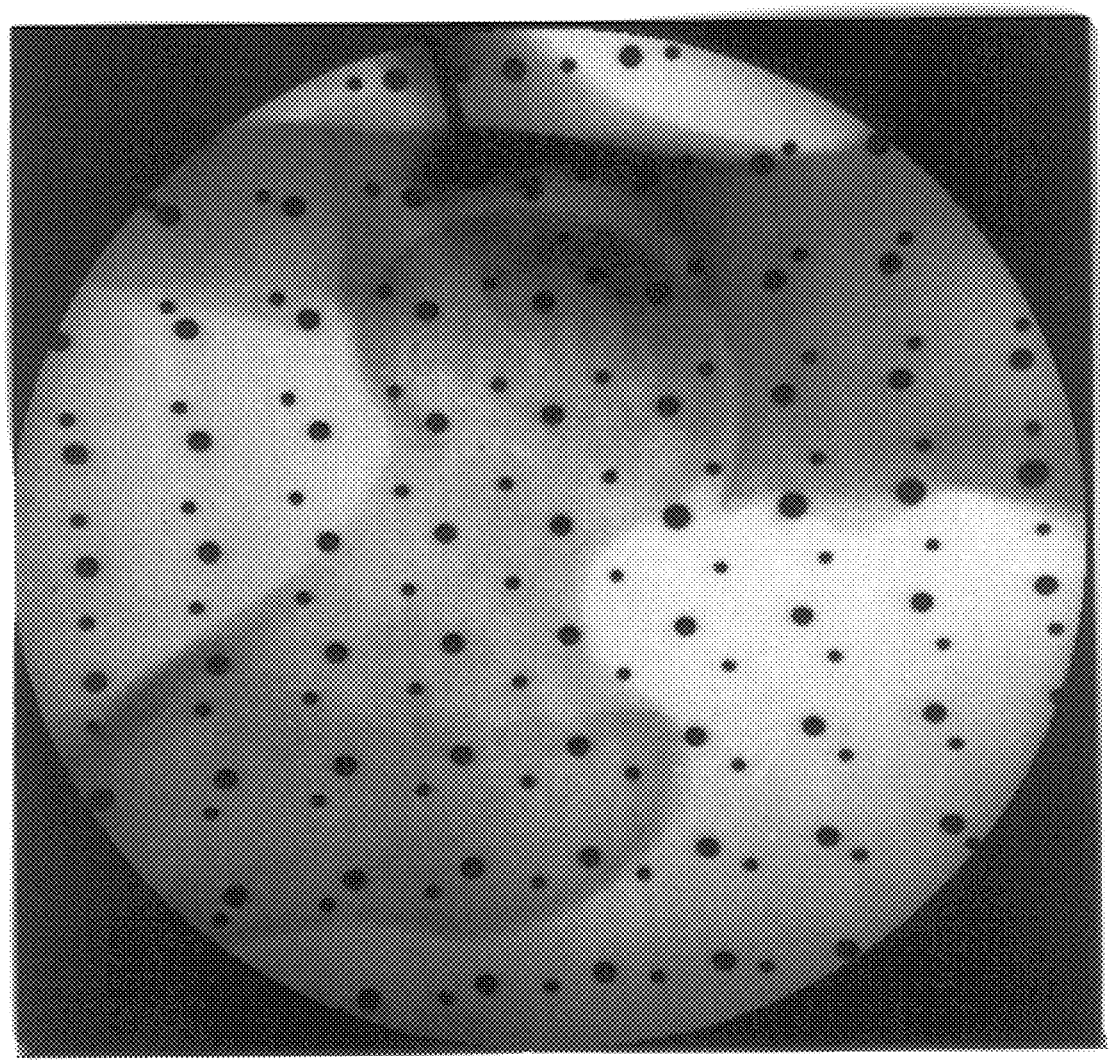
FIG. 7A is an image illustrating two-dimensional circular artifacts projected from spherical calibration markers.
Figure 7B:
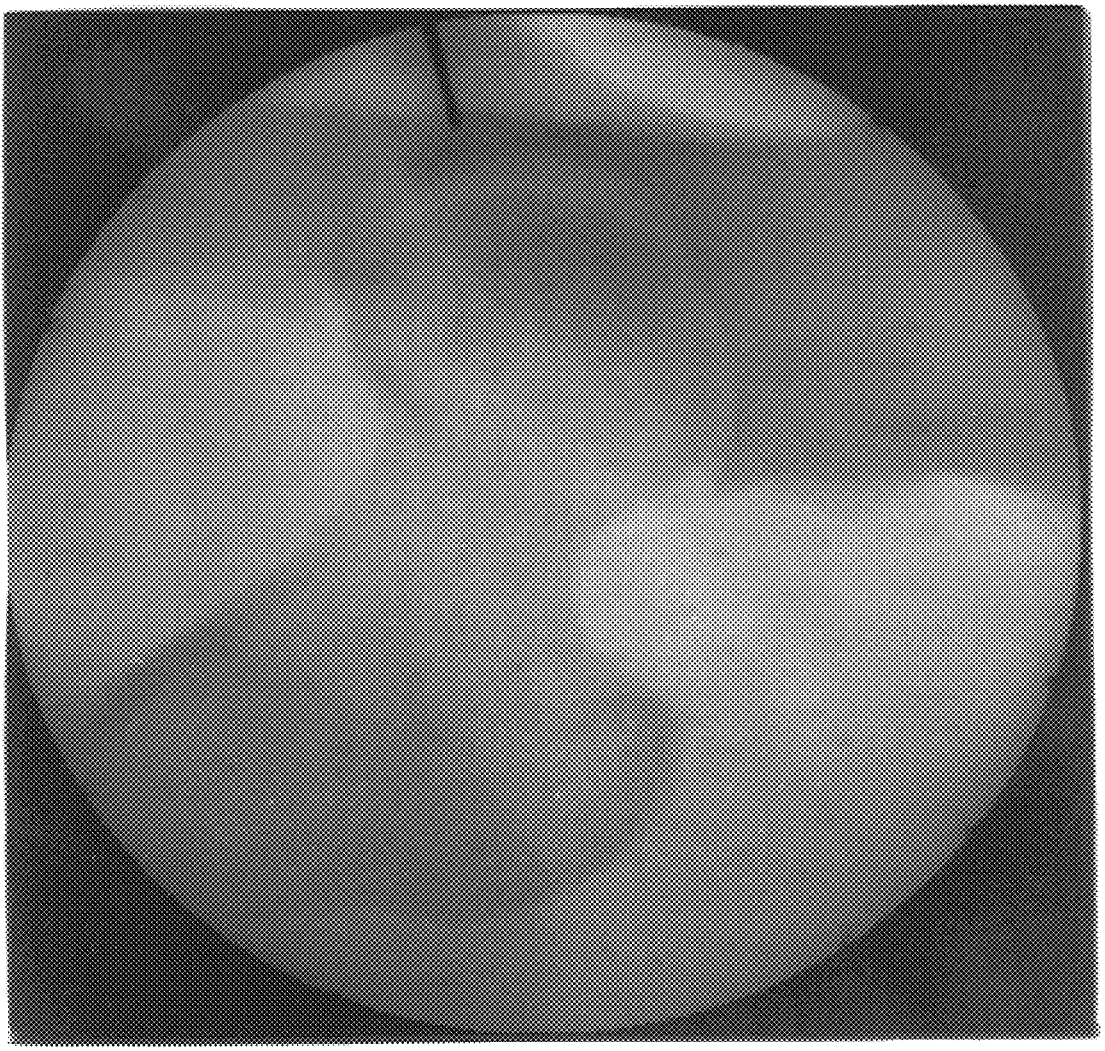
FIGS. 7B and 7C are versions of the image shown in FIG. 7A after application of methods consistent with the present invention.
Figure 7C:
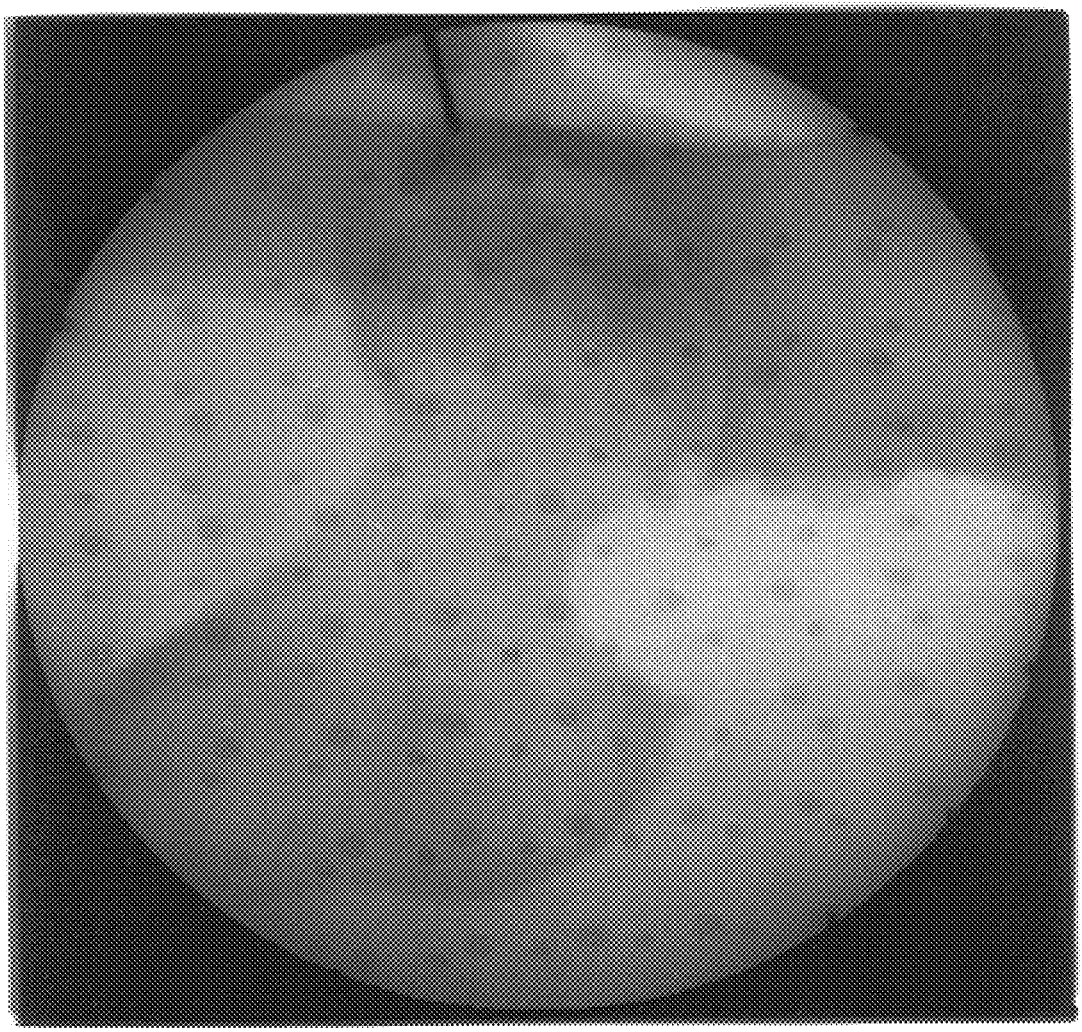

In a first method, processor 303 simply calculates the average intensity value of surrounding pixels 601 (i.e., the sum of the surrounding pixel values divided by the number of surrounding pixels in the sample) and sets each of the pixels in marker projection 604 to that intensity value. FIG. 7A is an image, similar to image 400, having two-dimensional circular artifacts projected from spherical calibration markers. FIG. 7B is an image after application of the averaging method applied to the image of FIG. 7A. FIG. 7C is the image shown in FIG. 7B after application of the averaging method and the addition of a small constant offset chosen to make the marker projection visibly distinct but not visibly distracting.

Figure 8:
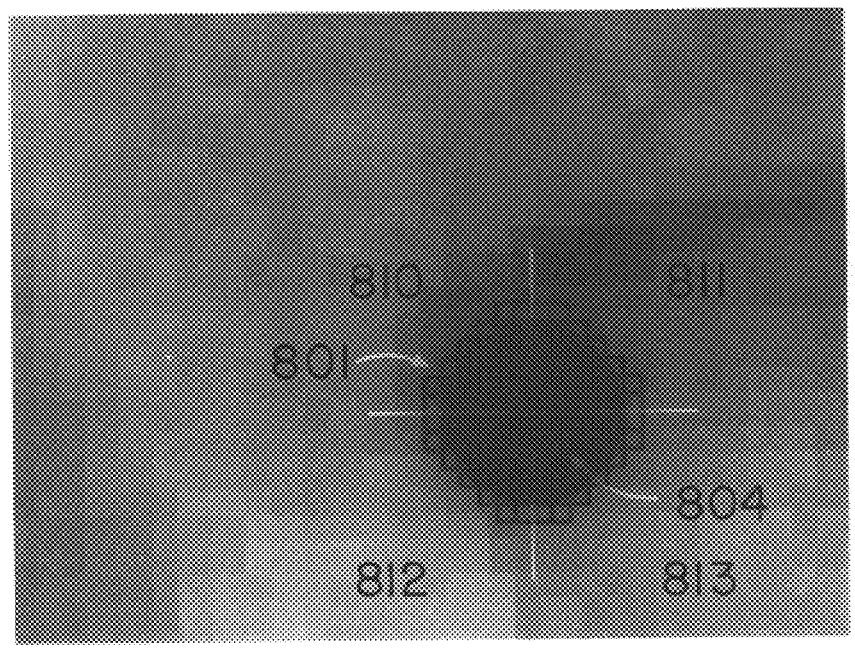
FIG. 8 is an image of a calibration marker projection divided into four regions.

In a second method, processor 303 divides marker projection 604 into multiple regions and separately calculate average intensity values of surrounding pixels for each region. An example of a marker projection divided into four regions (quadrants) is shown in FIG. 8. Marker projection 804 is surrounded by pixels 801. Processor 303 separately calculates the average value of the surround pixels in each of quadrants 810–813 and then sets the marker projection pixels in that quadrant to the calculated value.

Other methods, in addition to the average and multiple region averaging methods discussed above, may also be used to calculate new marker projection pixel values. In particular, a second general class of approaches for determining underlying marker projection intensity values uses estimators that optimize a criterion function in order to derive the pixel intensities. This class of methods involves maximum likelihood estimators such as the Expectation Maximization (EM) algorithm, neural networks, fuzzy systems, and other methods which estimate a set of parameters (i.e., the new marker projection intensity values) by maximizing a criterion function. For example, an EM algorithm could estimate underlying pixel intensities in a statistically optimal sense given the measured image and the current marker location. Any of these approaches may incorporate statistical models of the image that mathematically describe the expected image structure (e.g., measures of image texture or image variation, measures of feature orientation, etc.).

Artifact Elimination

Consistent with a second aspect of the present invention, artifacts introduced into an x-ray image by semi-transparent markers may be substantially eliminated while preserving much of the true underlying image.

The semi-transparent calibration markers should be opaque enough so that they are visible enough to be automatically identified in the x-ray images, and transparent enough so that the features underlying the markers (i.e., the features along the x-ray projection path passing through the markers) will also influence the image intensity. When these conditions are satisfied, the marker projections may be completely eliminated while preserving the underlying image features by subtracting offset values from the detected marker projections.

The semi-transparent calibration markers may be made from a material such as a thin layer of copper (e.g., 0.5–2 mm thick) or a solid ceramic layer.

Figure 9:
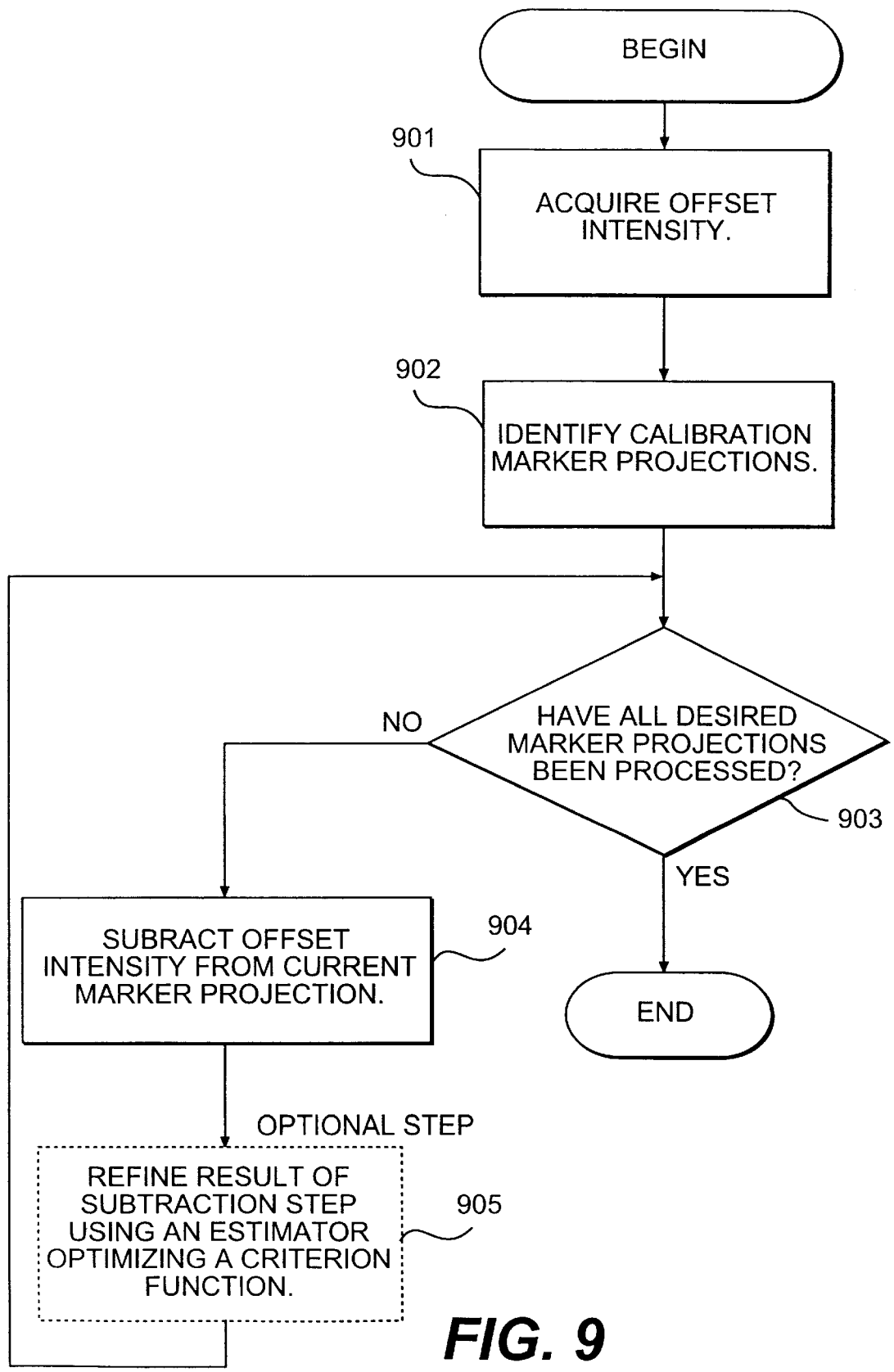
FIG. 9 is a flow chart of image processing methods consistent with the present invention for eliminating artifacts caused by semi-transparent calibration markers.

FIG. 9 is a flow chart of image processing methods consistent with the present invention for substantially eliminating artifacts caused by semi-transparent calibration markers.

Essentially, artifact elimination is performed by subtracting a pre-measured offset from each pixel in the marker projections. The appropriate offset value to subtract is initially determined by processor 303 by acquiring an intensity image of a calibration marker projection in which no anatomy or other material is visible (step 901). That is, a preselected calibration marker is placed in an x-ray imaging path in which the x-rays pass only through the calibration marker. If all the pixels corresponding to the preselected calibration marker are of the same intensity, then the offset is simply that intensity value. If the intensity values of the pixels corresponding to the preselected calibration marker projection vary, whether by design or because of consistent variance in the calibration marker's material composition, then a separate offset value may be saved for each pixel.

Once the offset for a particular image has been determined, processor 303 proceeds with eliminating the artifacts by identifying the calibration marker projections, (step 902), and, for each identified projection, (step 903), subtracting the acquired offset(s) from the pixels of the projection (step 904). Ideally, steps 901–904 will completely eliminate the artifacts from the image while leaving the true underlying image (e.g., the patient anatomy). Practically, image noise may prevent a perfect result. In these situations, processor 303 refines the result by applying an estimator function, such as the EM algorithm described above, to further improve the result (optional step 905). The input to the EM algorithm is the output of step 904, while the output is a refined estimate of the true underlying pixel intensities.

Figure 10:
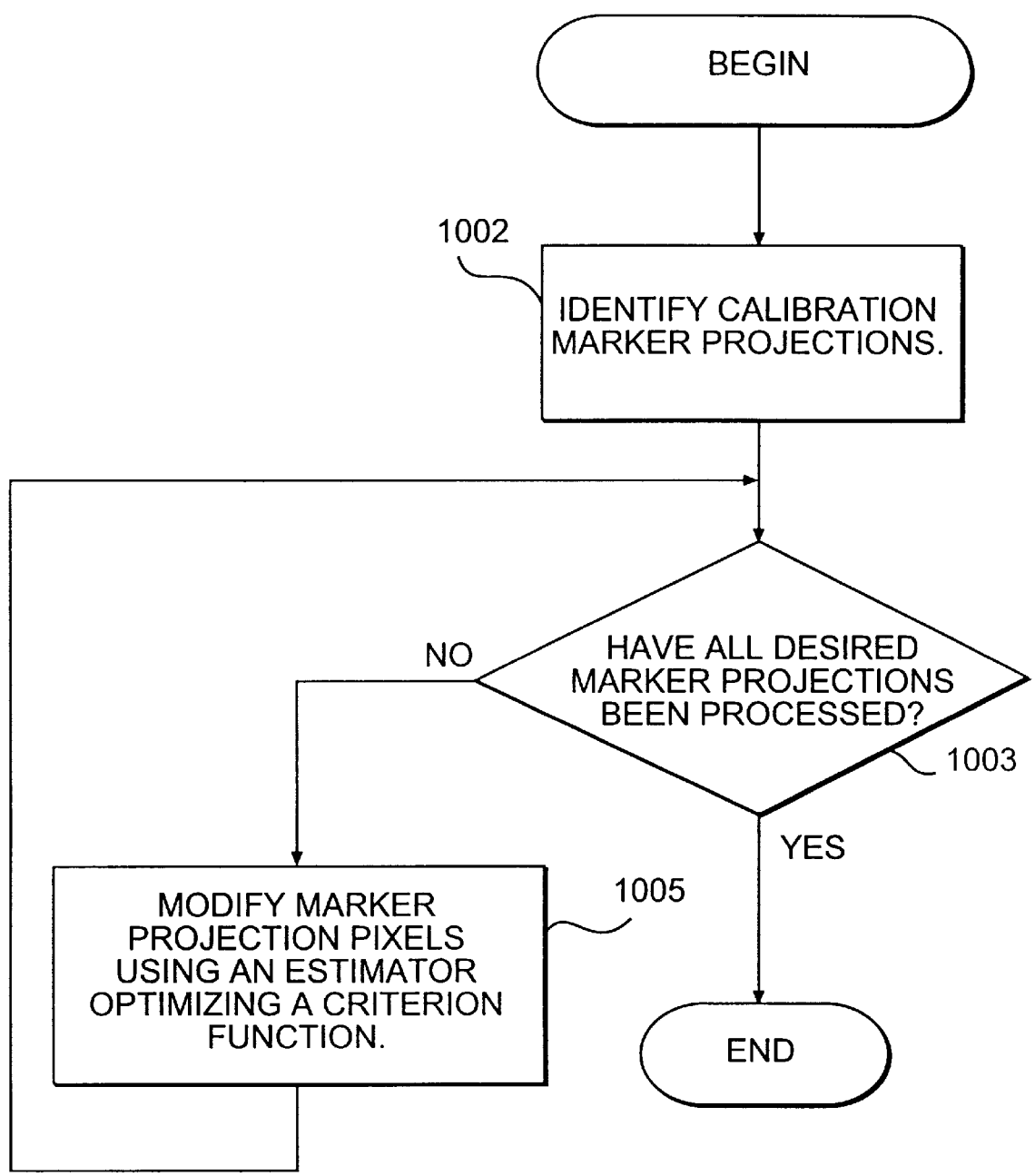
FIG. 10 is a flow chart of image processing methods consistent with a second aspect of the present invention for eliminating artifacts caused by semi-transparent calibration markers.

FIG. 10 is a flow chart of image processing methods consistent with a second aspect of the present invention for substantially eliminating artifacts caused by semi-transparent calibration markers. The process illustrated in FIG. 10 is similar to that illustrated in FIG. 9, except that instead of subtracting offset intensities from the pixels of the marker projections, an estimator optimizing a criterion function, such as the EM function, is used to modify the marker projections. More specifically, processor 303 eliminates, or substantially eliminates, the artifacts by identifying the calibration marker projections, (step 1002), and, for each identified projection, (step 1003), applies the estimator function (step 1005).

As described in this disclosure, artifacts present in x-ray images are de-emphasized. More particularly, artifacts may either be reduced in prominence (artifact reduction) or eliminated all together (artifact elimination), thereby improving the image presented to the clinician.

While there has been illustrated and described what are at present considered to be preferred embodiments and methods of the present invention, it will be understood by those skilled in the art that various changes and modifications may be made, and equivalents may be substituted for elements thereof without departing from the true scope of the invention. For example, although described in the context of a medical imaging system using x-rays, methods consistent with the present invention can be performed on any digitized input image.

In addition, many modifications may be made to adapt a particular element, technique or implementation to the teachings of the present invention without departing from the central scope of the invention. Therefore, it is intended that this invention not be limited to the particular embodiments and methods disclosed herein, but that the invention include all embodiments falling within the scope of the appended claims.

What is claimed:

1. A medical imaging system comprising:

an x-ray source for generating x-rays;

calibration markers positioned in a path of the x-rays;

an x-ray receiving device for receiving the generated x-rays and deriving a digital image representing objects through which the generated x-rays have passed, the digital image including representations of the calibration markers; and a processor coupled to the x-ray receiving device for performing image processing operations on the digital image, the image processing operations de-emphasizing the visual presence of the representations of the calibration markers.

2. The system of claim 1, wherein the x-ray receiving device further comprises an image intensifier and a charge coupled device (CCD) array for deriving the digital image from the x-rays.

3. The system of claim 1, wherein the calibration markers are opaque to the x-rays.

4. The system of claim 1, wherein the calibration markers are semi-transparent to the x-rays.

5. The system of claim 3, wherein the processor further includes means for identifying pixels in the digital image that surround the calibration markers and means for modifying the representations of the calibration markers based on the values of the pixels that surround the representations of the calibration markers.

6. The system of claim 5, wherein the processor further includes means for adding a constant offset to the modified representations of the calibration markers to enhance the visibility of the representations.

7. The system of claim 4, wherein the processor further includes means for acquiring an offset value corresponding to an intensity of one of the calibration marker representations in which the x-rays have not traversed the objects.

8. The system of claim 7, wherein the processor further includes means for subtracting the offset value from each of the calibration marker representations.

9. The system of claim 8, wherein the processor further includes means for refining the subtracted versions of the calibration marker representations by using an estimator algorithm that optimizes a criterion function.

10. The system of claim 1, wherein the processor de-emphasizes the visual presence of the representations of the calibration markers using a maximum likelihood estimator that maximizes a criterion function.

11. The system of claim 10, wherein the maximum likelihood estimator is an Expectation Maximizing algorithm.

12. A method of creating an image of an object comprising the steps of:

transmitting x-rays in a path including a target object and calibration markers arranged in a predetermined pattern;

receiving the transmitted x-rays;

deriving a digital image representing the object and the calibration markers; and de-emphasizing the representations of the calibration markers in the digital image.

13. The method of claim 12, wherein the step of transmitting the x-rays further includes the substep of transmitting the x-rays through semi-transparent calibration markers arranged in the predetermined pattern.

14. The method of claim 13, wherein the step of de-emphasizing the representations of the calibration markers includes the substep of eliminating the representations of the calibration markers by subtracting an offset from pixels in the digital image that comprise the calibration marker representations.

15. The method of claim 12, wherein the step of transmitting the x-rays further includes the substep of transmitting the x-rays to calibration markers opaque to the x-rays.

16. The method of claim 15, wherein the step of de-emphasizing the representations of the calibration markers includes the substep of identifying pixels in the digital image that surround the calibration markers and modifying the representations of the calibration markers based on the values of the pixels that surround the representations of the calibration markers.

17. The method of claim 16, further including the substep of adding an offset to the modified representations of the calibration markers to enhance the visibility of the representations.

18. A computer readable medium containing computer instructions for causing a processor to perform the steps of:

storing a digital image representing anatomy of a patient, the digital image including representations of calibration markers that at least partially occlude portions of the patient anatomy; and performing image processing operations on the digital image to de-emphasize the representations of the calibration markers.

19. The computer readable medium of claim 18, wherein the instructions for causing the processor to perform the step of de-emphasizing the representations of the calibration markers further include instructions for eliminating the representations of the calibration markers by subtracting an offset from pixels in the digital image that comprise the calibration marker representations.

20. The computer readable medium of claim 18, wherein the instructions for causing the processor to perform the step of de-emphasizing the representations of the calibration markers further include instructions for identifying pixels in the digital image that surround the calibration markers and modifying the representations of the calibration markers based on the values of the pixels that surround the representations of the calibration markers.

21. The computer readable medium of claim 20, further including instructions for adding an offset to the modified representations of the calibration markers to enhance the visibility of the representations.

22. The computer readable medium of claim 18, wherein the instructions for causing the processor to perform the step of de-emphasizing the representations of the calibration markers further include instructions for de-emphasizing the visual presence of the representations of the calibration markers using a maximum likelihood estimator that maximizes a criterion function.

23. The computer readable medium of claim 22, wherein the maximum likelihood estimator is an Expectation Maximizing algorithm.

24. A computer system comprising:

a first computer memory storing a digital image representing anatomy of a patient, the digital image including representations of calibration markers that at least partially occlude portions of the patient anatomy;

a second memory storing instruction for performing image processing operations on the digital image to de-emphasize the representations of the calibration markers; and a processor coupled to the first and second memory for executing the instructions stored in the second memory.

25. The computer system of claim 24, wherein the processor further includes means for identifying pixels in the digital image that surround the calibration markers and means for modifying the representations of the calibration markers based on the values of the pixels that surround the representations of the calibration markers.

26. The computer system of claim 25, wherein the processor further includes means for adding a constant offset to the modified representations of the calibration markers to enhance the visibility of the representations.

27. The computer system of claim 24, wherein the processor de-emphasizes the visual presence of the representations of the calibration markers using a maximum likelihood estimator that maximizes a criterion function.

28. The computer system of claim 27, wherein the maximum likelihood estimator is an Expectation Maximizing algorithm.

29. A method for causing a computer processor to perform the steps of:

storing a digital image representing anatomy of a patient, the digital image including representations of calibration markers that at least partially occlude portions of the patient anatomy; and performing image processing operations on the digital image to de-emphasize the representations of the calibration markers.

30. The method of claim 29, wherein the step of de-emphasizing the representations of the calibration markers includes the substep of eliminating the representations of the calibration markers by subtracting an offset from pixels in the digital image that comprise the calibration marker representations.

31. The method of claim 29, wherein the step of de-emphasizing the representations of the calibration markers includes the substep of identifying pixels in the digital image that surround the calibration markers and modifying the representations of the calibration markers based on the values of the pixels that surround the representations of the calibration markers.

32. The method of claim 31, further including the substep of adding an offset to the modified representations of the calibration markers to enhance the visibility of the representations.

33. A medical imaging system comprising:

an x-ray source for generating x-rays;

semi-transparent calibration markers positioned in a path of the x-rays;

an x-ray receiving device for receiving the generated x-rays and deriving a digital image representing objects through which the generated x-rays have passed, the digital image including representations of the calibration markers; and a processor coupled to the x-ray receiving device for performing image processing operations on the digital image, the digital processing operations removing distortion from the image by performing intrinsic calibration on the image based on projections of the semi-transparent calibration markers in the image.

* * * * *